United States Patent [19]

Witherow et al.

[11] Patent Number: 4,810,094
[45] Date of Patent: Mar. 7, 1989

[54] DUAL WAVELENGTH HOLOGRAPHIC INTERFEROMETRY SYSTEM AND METHOD

[75] Inventors: William K. Witherow, Huntsville, Ala.; Andreas Ecker, Hagnau, Fed. Rep. of Germany

[73] Assignee: The United States of America as represented by the Administrator of the National Aeronautics and Space Administration, Washington, D.C.

[21] Appl. No.: 149,822

[22] Filed: Jan. 29, 1988

[51] Int. Cl.[4] .............................................. G01B 9/025
[52] U.S. Cl. ...................................... 356/347; 356/361
[58] Field of Search ........................ 356/347, 348, 361

[56] References Cited

U.S. PATENT DOCUMENTS

| | | | |
|---|---|---|---|
| 3,758,187 | 9/1973 | Thomas et al. | 350/3.75 |
| 3,802,758 | 4/1974 | Havener et al. | 350/3.6 |
| 3,860,346 | 1/1975 | Kersch et al. | 356/348 |
| 4,428,675 | 1/1984 | Witherow | 356/347 |
| 4,597,630 | 7/1986 | Brandstetter et al. | 350/3.83 |

Primary Examiner—Davis L. Willis
Assistant Examiner—Matthew W. Koren
Attorney, Agent, or Firm—William J. Sheehan; John R. Manning; Charles E. B. Glenn

[57] ABSTRACT

The present invention relates to a two-wave holographic interferometry system and method. In such systems, a reference beam holographic is super-imposed on an object beam, the object beam being an image obtained by passing a beam through an object regarding which some parameter (e.g. temperature gradient) is to be measured. A photograph (50) of the superimposed beams (D) is taken. The present invention employs two object (B) and two reference (A) beams and the invention is particularly concerned with the use of a prism assembly (C) which causes the two different wavelengths (W1, W2) of the object beams to emerge from the prism at slightly different angles, thereby providing two holographic images which are slightly displaced from each other.

7 Claims, 1 Drawing Sheet

DUAL WAVELENGTH HOLOGRAPHIC INTERFEROMETRY SYSTEM AND METHOD

ORIGIN OF THE INVENTION

The invention described herein was made inpart by employees of the United States Government and may be manufactured and used by or for the Government for governmental puposes without the payment of any royalties thereon or therefor.

BACKGROUND OF THE INVENTION

Holographic interferometry is used to study fluid flow phenomena. Gradients in the fluid can be caused by temperature variations, concentration variations, or a combination or the two. Holography with one wavelength cannot distinguish between the two types of variations. Holography with two wavelengths can be used to determine gradients caused by each of the two types of variations. This is done by comparing the two images that are obtained from the two wavelengths. The difference in fringe spacing from the images can be manipulated mathematically to determine whether the gradients were caused by concentration or temperature variations. At present, the two images are obtained by reconstructing the hologram with the first wavelength and taking a photograph, then reconstructing with the second wavelength to obtain a second photograph. Both images are recorded and overlapped simultaneously on the holographic film. Since the difference in fringe spacing in some cases can be very small, great care must be exercised in obtaining and recording the individual photographs.

U.S. Pat. No. 3,860,346 discloses the use of adjustable mirrors in real-time holographic interferometry to change the position of the reference beam relative to the object beam. U.S. Pat. No. 3,802,758 discloses a holographic system wherein a dual hologram holder is used to adjust the position of one hologram relative to the other. U.S. Pat. No. 3,758,187 discloses a holographic system wherein a rotating polygon mirror is used to adjust the position of a reference beam. U.S. Pat. No. 4,597,630 discloses the use of a dove prism to split an object beam into two beams in a holography system. U.S. Pat. No. 4,428,675 discloses a double-exposure system.

However, the prior art does not disclose the expedient of a prism system to modify the positions of a pair of object beams in a dual-beam holographic interferometry system. This causes the images on the hologram during reconstruction. Then during reconstruction the two images will be displaced enough so that one large format photograph may be taken that will contain both images.

SUMMARY OF THE INVENTION

Two laser beams of different wavelengths are aligned and passed through a cube beamsplitter. The wavelengths for one experiment were 632.8 nm and 442.0 nm. The beamsplitter separates each of the two beams into a reference beam and an object beam. Both the reference beams and the object beams are then spatially filtered and collimated. The reference beams are made to be incident on the holographic film. The object beams pass through the test cell which contains the fluid experiment. The object beams then pass through a prism assembly that causes the two wavelengths of the object beam to emerge from the prisms at slightly different angles. The two object beams are then incident on the holographic film where the hologram is made. The prism assembly can be modified to achieve different separations of the images. Since both photographs are taken simultaneously, the sensitivity of the system is greatly improved.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
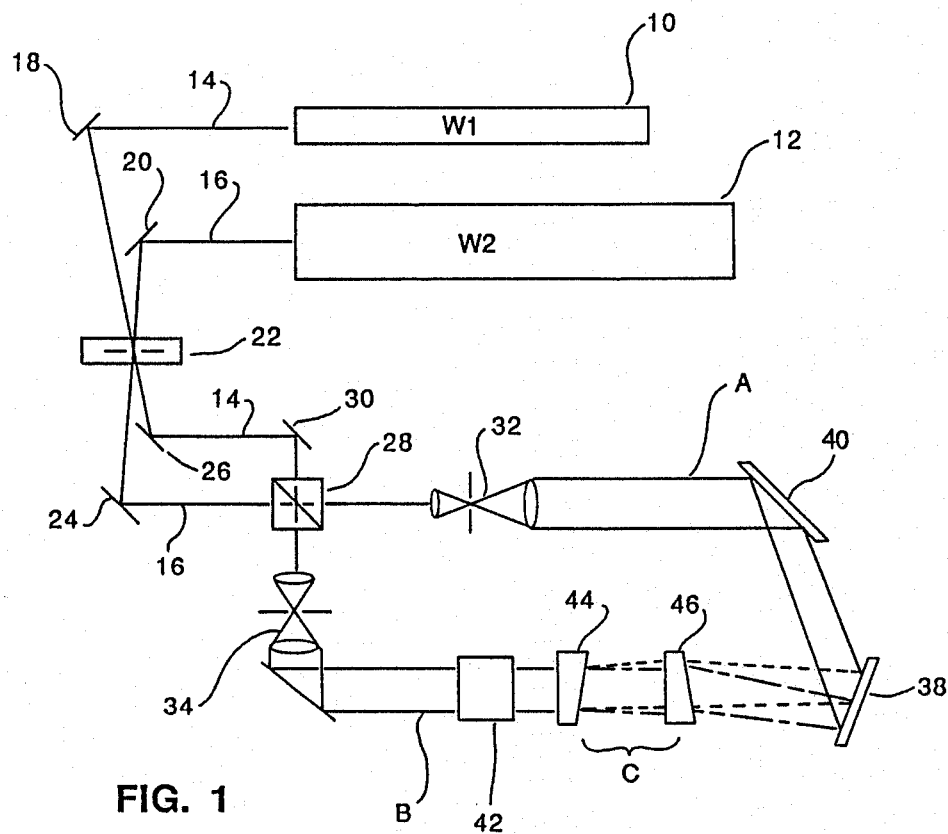
FIG. 1 is a schematic view illustrating a dual wavelength holographic interferometry method in accordance with the invention.
Figure 2:
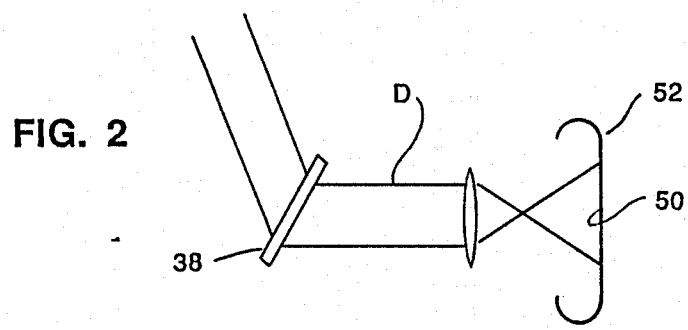
FIG. 2 is a schematic view illustrating the reconstruction of a hologram from a dual wavelength holographic interferometry method in accordance with the invention.

Referring now in more detail to the drawings, a pair of lasers 10 and 12 generate aligned parallel beams 14 and 16 respectively. The wavelength of laser beam 14 is different from the wavelength of laser beam 16. In one example, wavelengths of $W1 = 632.8$ nm and $W2 = 442.0$ nm were utilized. For this purpose, any suitable lasers may be utilized at 10 and 12, such as a helium-neon laser and a argon laser. Beams 14 and 16 are reflected by mirrors 18 and 20 and are directed through a shutter 22 to redirecting mirrors 24 and 26 which pass the beams through a conventional cube beamsplitter 28. For this purpose, a second redirecting mirror 30 is provided for laser beam 14. The beamsplitter separates each of the beams 14 and 16 into a reference beam A containing the two wavelengths and an object beam B containing the two wavelengths. The split beams emerging from the beamsplitter are first passed through spacial filters 32 and 34 respectively. Filters 32 and 34 spatially filter and collimate the split beams. The reference beams A are directed to holographic film 38 by means of a reflecting mirror 40. The object beams B are passed through a test cell 42 which contains the fluid experiment. The object beams then pass through a prism assembly C that causes the two wavelengths of the object beam to emerge from the prisms at slightly different angles. The two object beams are then incident on holographic film 38 where the hologram is made. Prism assembly C includes two conventional prisms 44 and 46 which may be arranged and modified to achieve different separations of the images. The prism assembly C causes the images created by each wavelength to be slightly displaced on the hologram during reconstruction. During reconstruction, the two images will be displaced sufficiently that a large format photograph may be taken containing both images. Referring to FIG. 2, large format picture 50 is illustrated as being taken of the superimposed reference and object beams D of hologram 38. This may be done by any suitable camera 52.

In accordance with the invention, a method of manipulating holographic images on holographic film for improving the accuracy of data reduction is disclosed.

The method includes generating first and second aligned laser beams 14 and 16 having different wavelengths W1 and W2. The beams are passed through cube splitter 28 and separated into a reference beam having two different wavelengths and an object beam having the two different wavelengths. The beams are filtered and collimated. The reference beam is incident upon the holographic film. The object beam is passed through a test cell containing a fluid experiment. Next, the object beams are passed through a prism assembly causing the different wavelengths of the object beams to emerge from the prism assembly at slightly different angles. The object beams passing through the test cell are then made incident upon the holographic film in a manner that the images created by the different wavelengths are displaced enough so that one large format photograph may be taken containing both images which are highly distinct and perceptible. In this manner, holographic images are manipulated for improving the accuracy of data reduction to study fluid flow phenomena. The differences in displacement and fringe spacing of the images can be manipulated mathematically to study the concentration of temperature variations.

While a preferred embodiment of the invention has been described using specific terms, such description is for illustrative purposes only, and it is to be understood that changes and variations may be made without departing from the spirit or scope of the following claims.

What is claimed is:

1. A method of manipulating holographic images on holographic film for improving the accuracy of data reduction comprising:
   generating first and second aligned laser beams having different wavelengths;
   passing said first and second aligned beams through a cube beam splitter;
   separating said first and second beams into respective first and second reference beams of said different wavelengths and first and second object beams of said different wavelengths;
   filtering and collimating said reference and object beams;
   passing said first and second reference beams incident upon holographic film;
   passing said first and second object beams through a test cell containing a fluid experiment;
   passing said first and second object beams through a prism assembly causing the two wavelengths of said first and second object beams to emerge from said prism assembly at slightly different angles; and
   directing said first and second object beams incident upon said hologram film in a manner that the images created by said first and second wavelengths are displaced so that a single format photograph may be taken containing both images which are visually distinct and perceptible.

2. A method of manipulating holographic images on holographic film for improving the accuracy of data reduction of the type which includes generating a pair of aligned laser beams having different wavelengths and separating said beams into respective first and second reference beams and first and second object beams of said different wavelengths wherein the improvement comprises:
   passing said first and second reference beams onto said holographic film;
   passing said first and second object beams through a test cell containing a fluid experiment;
   passing said first and second object beams through a prism assembly causing the two wavelengths of said first and second object beams to emerge from said prism assembly at slightly different angles; and
   directing said first and second object beams incident upon said hologram film in a manner that the images created by said first and second wavelengths are displaced so that a single format photograph may be taken containing both images which are visually distinct and perceptible.

3. The method of claim 2 including passing said first and second aligned beams through a cube beamsplitter to separate said beams.

4. The method of claim 2 including filtering and collimating said reference and object beams.

5. A method of manipulating images on holographic film for improving the accuracy of data reduction comprising:
   creating first and second reference beams and first and second object beams having different wavelengths;
   passing said first and second reference beams incident upon holographic film;
   passing said first and second object beams through a test cell containing a fluid experiment;
   passing said first and second object beams through a prism assembly causing the two wavelengths of said first and second object beams to emerge from said prism assembly at slightly different angles; and
   directing said first and second object beams incident upon said hologram film in a manner that the images created by said first and second wavelengths are displaced so that a single format photograph may be taken containing both images which are visually distinct and perceptible.

6. The method of claim 5 including filtering and collimating said reference and object beams.

7. A system for manipulating holographic images on holographic film for improving the accuracy of data reduction comprising:
   first and second lasers for generating first and second aligned laser beams having different wavelengths;
   a cube beam splitter means through which said first and second aligned beams are passed for separating said first and second beams into respective first and second reference beams of said different wavelengths and first and second object beams of said different wavelengths;
   means for filtering and collimating said reference and object beams;
   holographic film upon which said first and second reference beams are made incident;
   a test cell through which said first and second object beams are passed containing a fluid experiment;
   a prism assembly means through which said first and second object beams are passed causing the two wavelengths of said first and second object beams to emerge from said prism assembly means at slightly different angles; and
   means for directing said first and second object beams incident upon said hologram film in a manner that the images created by said first and second wavelengths are displaced so that a single format photograph may be taken containing both images which are visually distinct and perceptible.

* * * * *